US006733437B2

(12) United States Patent
Mackin et al.

(10) Patent No.: US 6,733,437 B2
(45) Date of Patent: May 11, 2004

(54) NON-HAND CONTACT ALARM SILENCE SYSTEM FOR INFANT CARE APPARATUS

(75) Inventors: Michael H. Mackin, Ellicott City, MD (US); Christopher A. Dykes, Columbia, MD (US)

(73) Assignee: Datex Ohmada, Inc., Madison, WI (US)

( * ) Notice: Subject to any disclaimer, the term of this patent is extended or adjusted under 35 U.S.C. 154(b) by 0 days.

(21) Appl. No.: 10/119,284

(22) Filed: Apr. 9, 2002

(65) Prior Publication Data

US 2003/0191358 A1 Oct. 9, 2003

(51) Int. Cl.[7] ............................................ A61B 11/00
(52) U.S. Cl. ..................................................... 600/22
(58) Field of Search ............................ 600/21–22, 300; 128/736; 728/897, 892

(56) References Cited

U.S. PATENT DOCUMENTS 3,675,051 A * 7/1972 Mioduski .................... 327/205
5,115,567 A * 5/1992 Yang et al. ................. 606/172
5,382,791 A 1/1995 Leff et al.
5,474,517 A 12/1995 Falk et al.
5,912,624 A 6/1999 Howard
5,954,225 A 9/1999 Powe
6,161,655 A 12/2000 Lejon et al.
6,245,010 B1 6/2001 Jones
6,296,606 B1 * 10/2001 Goldberg et al. ............ 600/22

FOREIGN PATENT DOCUMENTS

EP 1074957 A 2/2001

* cited by examiner

*Primary Examiner*—Samuel G. Gilbert
(74) *Attorney, Agent, or Firm*—Roger M. Rathbun

(57) ABSTRACT

A patient care apparatus and method where the apparatus has an audible sound producing device that sounds an audible alarm when a particular alarm condition is sensed with respect to a patient or the apparatus itself. The apparatus includes a non-hand contact alarm silence switch that can be activated to silence the audible alarm. That non-hand contact alarm silence switch can be activated by various means that do not involve an object or person actually contacting the switch by any portion of the care provider that would be expected to remain in sterile conditions. Various technologies can be used for the non-hand contact alarm silence switch including proximity sensing, optical sensing, temperature sensing, air pressure sensing or voice command, any one of which can activate the switch without the need to make physical contact of the alarm silence switch by a person or object. In one embodiment, the apparatus has a foot-operated alarm silence switch.

23 Claims, 2 Drawing Sheets

NON-HAND CONTACT ALARM SILENCE SYSTEM FOR INFANT CARE APPARATUS

BACKGROUND

The present invention relates to a patient care apparatus and, more particularly, to an infant care apparatus of the type that provides a support or bed for the infant as well as a means of warming the infant to aid in the wellbeing of that infant.

In the use of infant warmers, there is generally a support underlying the infant as well as some overhead heater, generally a radiant heater, that produces warmth to the infant by directing a pattern of infrared energy toward that infant. As a normal component or function of such infant warmers, there are various alarms that produce an audible sound when one of the alarm conditions has been sensed. With the presence of such audible alarms, there is normally also an alarm silence button or switch that allows the care provider to temporarily silence the alarm, it only being of importance with some alarms that the care provider be aware of the existence of an alarm condition and the care provider then can have the option of merely silencing the alarm after being adequately warned of the alarm condition. The activation of the alarm silence button also normally resets a timer within the patient care apparatus so that the audible alarm cannot be permanently silenced but will again cause an audible sound if the alarm condition persists unabated so that the care provider must again take some positive step to push the alarm silence button to cease that audible sound.

As an example, one typical alarm in the use of infant warmers is a pre-heat alarm and concerns the amount of energy supplied to the heater during a warm-up period. Generally, the care provider, in the manual mode of an infant warmer, can manually select from 0 to 100 percent of the rated capacity of the heater during the warm up period. If the care provider sets the heater at above 25 percent, there will be an alarm after a predetermined period of elapsed time at that setting, typically about 15 minutes, at which point the audible alarm sounds as a warning to the care provider. Whatever the source of the alarm, it is normally necessary for the caregiver to manually push the alarm silence button on or near the particular apparatus to silence that alarm so as to take some action in response to the alarm condition or to merely note the existence of the alarm condition and silence that audible sound.

In many instances, the care provider is, at that time, attending to the mother to be in the same room and is operating in a sterile environment, that is, the care provider is wearing gloves that must be maintained in a sterile condition. In such instances, the sterile environment is maintained by the caregiver wearing a gown and with gloves that overlap the sleeves of the gown so that almost the entire upper body of the caregiver is maintained in sterile conditions. Thus, any touching of an alarm silence button by any portion of the caregivers upper body, that is, any portion of the body above the waist, can destroy the sterility of the caregiver and it is, of course, therefore, fully expected, and indeed required, that a considerable portion of the caregiver's body be maintained in the sterile conditions.

Accordingly, when the audible alarm sounds on the infant warmer, it becomes necessary for the care provider to silence the alarm to prevent the annoyance of a continuous audible alarm and therefore must remove the sterile gloves, push the alarm silence switch or button, and then re-glove to return to attending to the patient then in the birthing process or undergoing some other procedure requiring the sterile conditions. The normal alarm silence button thereby silences the audible alarm, however, it also resets an alarm clock such that the same alarm will again be activated within that reset predetermined time period and the audible alarm will again sound such that the care provider must go through the same procedure again. As such, once silenced, the caregiver is likely to have to repeat the procedure again to maintain that alarm silence.

As can be seen, the overall procedure of carrying out the alarm silence is therefore burdensome, annoying and constitutes an interruption in the continual care that is needed during a rather critical time period in providing care to the patient giving birth. Alternatively, other alarms may be similarly affected, for example there is also normally an alarm that activates an audible sound in the event the skin temperature of the infant is higher or lower by a certain temperature range of a control temperature, that is, the alarm may sound in the event the temperature of the infant is above or below the control temperature by 1 degree Centigrade. Such alarms can therefore activate when the care provider is actually busy working on the infant and, again, the care provider has to remove the gloves that are under sterile conditions, manually push the alarm silence button on the infant warmer control panel and then re-glove to continue with the particular procedure on the infant.

Other bothersome scenarios are, of course, possible such as when the care provider is in a room with a number of infant warmers and is actively carrying out a procedure on an infant when an audible alarm is activated on one of the other infant warmers in that room. That care provider thus has to go over to the other infant warmer and proceed with the steps of removing gloves, manually pushing the alarm silence button and then re-gloving to return to the infant to continue attending to the infant. As also can be seen the problem is not limited to the use of an infant warmer, but is equally applicable to other types and kinds of infant equipment or adult equipment, medical monitors and the like, that is, to a wide variety of environments where a care provider is carrying out some procedure on a patient under sterile conditions.

There is, therefore, clearly a need for some type of alarm silence switch that can be activated to silence an audible alarm that does not require a person to use ones hand or hands to physically push a button or switch in order to carry out that function.

SUMMARY OF THE INVENTION

Accordingly, the present invention relates to a alarm silence switch that can be activated by means other than by using ones hands so that the care provider, in any relevant environment, can silence the audible alarm of the particular piece of apparatus and reset the alarm time without the need to remove gloves and to re-glove after the alarm silence function has been carried out. The present invention will be described with respect to an infant warmer, however, it can be seen that the present invention can be used in other infant care equipment or adult care equipment, such as medical monitors and to any environment where the care provider is gloved and working in a sterile surrounding so that the need for the hereinbefore described process of de-gloving and re-gloving is necessary.

In the present invention, therefore, there is provided a means to carry out the normal alarm silence function without actually using the hands of a person, or for that matter, any portion of the caregivers body above the waist, to activate a button or switch and, therefore, is a means wherein the care provider can silence the alarm without the need to remove gloves and go through the entire process of re-gloving and interrupting whatever procedure is being undertaken at the time by that care provider.

In carrying out the present invention, in one embodiment there is a non-contact switch or means to silence the alarm and may include various different types of switches to carry out that purpose. For example, the present invention may utilize a proximity switch or sensor that can be activated by merely passing ones hand in front of or in close proximity to the sensor located on the piece of medical apparatus. Such proximity sensors are commonly available and may operate on the basis of optical sensing, radar, temperature detection or some other technology that is capable of sensing the close proximity of a person's hand to the sensor. By such sensing, therefore, the care provider can simply wave in front of the sensor to activate the alarm silence function without removing gloves from that hand while maintaining the sterile conditions of the hands.

Other technologies include the use of an air pressure or air flow sensor that detects a change in air pressure or flow created by the care provider blowing into the sensor at an area of the control panel i.e. activated by the motion of air or even a voice activated sensor that can be activated by the recognition of a word, such as "silence" or to a human voice exceeding a certain threshold such that the care provider can simply use verbal commands or sounds to activate the alarm silence function without the use of the hands.

As another embodiment, there is a foot activated alarm silence switch that can be physically touched by the foot of the care provider so as to silence the audible alarm without having to compromise the sterile conditions of the care provider in the region of the upper body, that is, above the waist of that care provider.

Additional features and advantages of the invention will become apparent to those skilled in the art upon consideration of the following detailed description of preferred embodiments exemplifying the best mode of carrying out the invention.

DETAILED DESCRIPTION OF THE INVENTION

Figure 1:
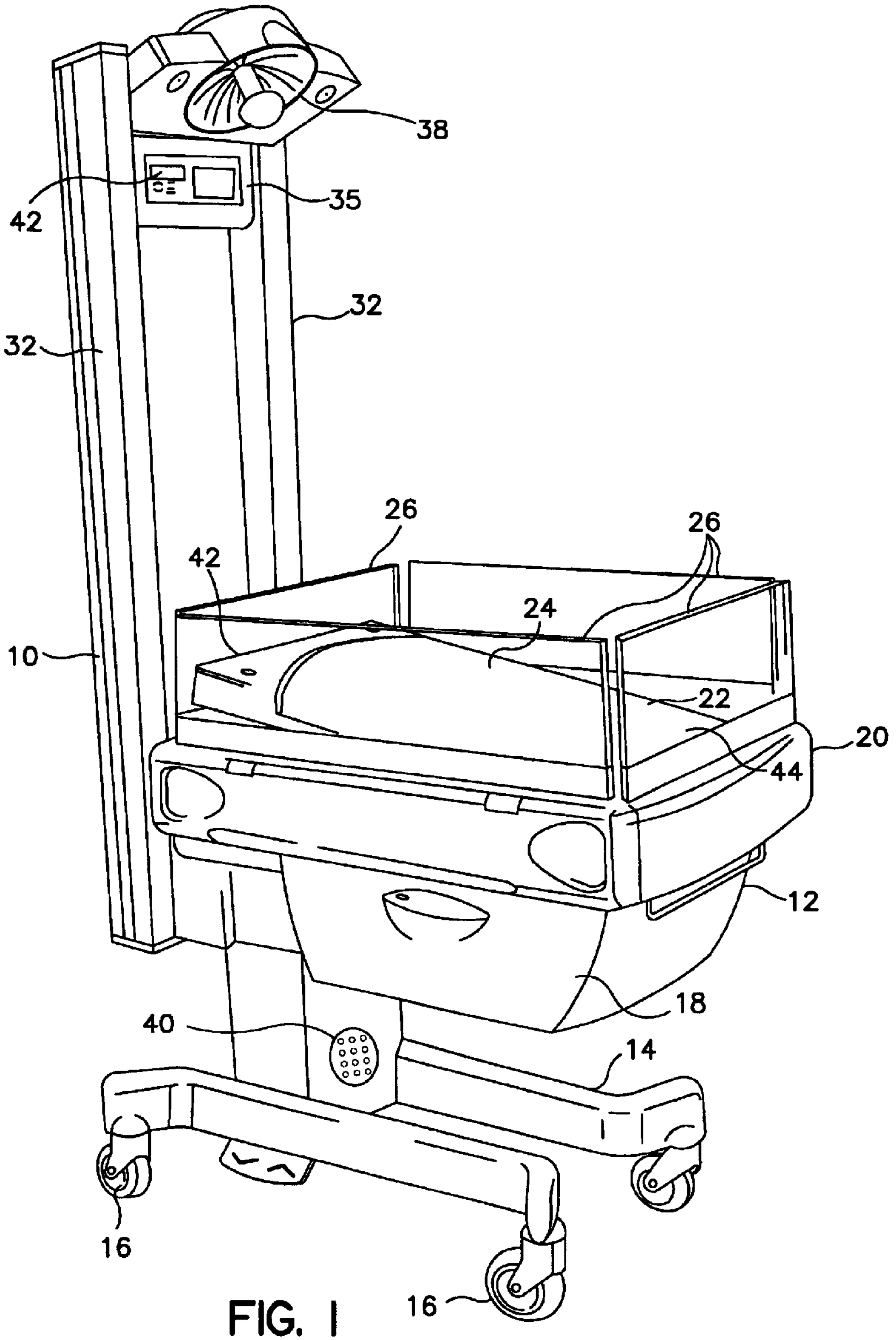
FIG. 1 is a perspective view of an infant warmer that is adapted for use with a non-hand contact switch constructed in accordance with the present invention.

Referring now to FIG. 1, there is shown an isometric view of an infant care center having a radiant heater to provide warmth to an infant contained within that center. As shown, the infant care center includes a frame 10 that supports the radiant heater and the controls that operate and monitor the infant care center. The frame 10 is supported upon a cabinet 12 which, in turn, is mounted upon a base 14 having wheels 16 so that the infant care center is easily movable. The cabinet 12 may also include one or more drawers 18 for containing items for attending to the infant.

An infant pedestal 20 is mounted atop of the cabinet 12 and on which is located an infant bed 22 which underlies an infant positioned thereon. Pedestal 20 is the main support for infant bed 20. The infant bed 22 has a generally planar upper surface 24 with appropriate cushioning material for comfort of the infant and further may be surrounded by guards 26, generally of a clear plastic material, and which contain the infant on the upper surface 24. In the usual infant care center, the guards 26 are removable and/or releasable for complete access to the infant.

Frame 10 includes a pair of vertical struts 32 that provide support for the upper structure of the infant care center. Mounted in between the vertical struts 32 at the upper area of the infant care center, there is located a control module 35 for containing the various electrical controls to operate the infant care center. In addition, a heater 38 is mounted to the vertical struts 32. As will be noted, the location of the heater 38 is positioned to be above the infant bed 22 and at the head end of the infant care center such that the heater 38 is focused so as to provide a radiant footprint on and around the infant to optimize the amount of heat directed upon the infant. Various types of focusable heaters are available for such application, examples of which may be a tubular metallic focused heater, a corrugated foil heater as shown and described in U.S. Pat. No. 5,474,517 or a specially constructed heater having a shape of a quadratic surface of revolution such as is shown and described in U.S. Pat. No. 6,245,010 B1 and assigned to the present assignee.

As is also shown in FIG. 1, there is an audible sound producing device 40 such as a speaker, so that an audible sound is produced upon the presence of an alarm condition. As previously indicated, there may be a variety of alarm conditions that are continuously monitored by the alarm system of the infant care center and an electronic circuit sends a signal to the audible sound producing device 40 upon the sensing of any of the number of potential alarm conditions. The audible sound producing device 40 is preferably, but not necessarily, located underneath the infant pedestal 20 so that the sound from that device is minimized as to its impact on an infant while still providing adequate notice to the care provider of the presence of an alarm condition. That feature of locating the sound producing device 40 in the aforedescribed location is shown and described in co-pending U.S. patent application Ser. No. 09/503,070, filed Feb. 12, 2000 and assigned to the assignee of the present patent application, and the disclosure of which is incorporated herein by reference.

A non-hand contact alarm silence switch 42 is also provided and which is preferably located in the control module, although it can be in any convenient location that is readily accessible to the care provider as will be seen. As will be noted, one alternate location would be in the base of the infant care center in the foot operated embodiment or other lower location that can be reached by the foot of the care provider. As stated, the non-hand contact alarm silence switch 42 may, in the first embodiment, be based upon a variety of technologies that all can activate a switch or provide a signal without requiring the actual contact with the switch, that is, the non-hand contact alarm silence switch 42 may be a proximity switch that is activated by the presence of some object within its sensitive area and may utilize optical sensing, radar, temperature or some other technology to sense the hand or other object passing in front of the non-hand contact alarm silence switch 42.

In addition, the non-hand contact alarm silence switch 42 could be operated by a change in air pressure or flow sensor such as by the care provider blowing in the active area of an air pressure sensor, that is, activated by some motion of air. As a further alternative, the non-hand contact alarm silence switch 42 can be a voice activated device that can be as sophisticated as recognizing a specific command from the care provider such as by saying the word "silence" or a more simple scheme such as recognizing a human voice sound above a certain threshold.

In any event, the non-hand contact alarm silence switch 42 is, in this embodiment, activated without the need to have any actual contact by the care provider and therefore that care provider can silence the alarm and start the internal timer without having to remove the sterile gloves, physically push a button and then re-glove to return to whatever procedure is then being carried out by that care provider. In this embodiment, it is noted that the care provider can move a hand to be positioned within the active area of the non-hand contact alarm switch 42 or an object can be carried in the hand to so activate that non-hand contact alarm silence switch 42.

In an alternate or second embodiment of the present non-hand contact alarm silence switch, there is a foot operated switch 43 located on or near the base of the infant care center and which is in a convenient location so that the care provider can easily activate the foot operated switch 43 with the foot, thereby still not affecting the sterility of any portion of the care provider's body above the waist where the sterile conditions must be maintained.

Figure 2:
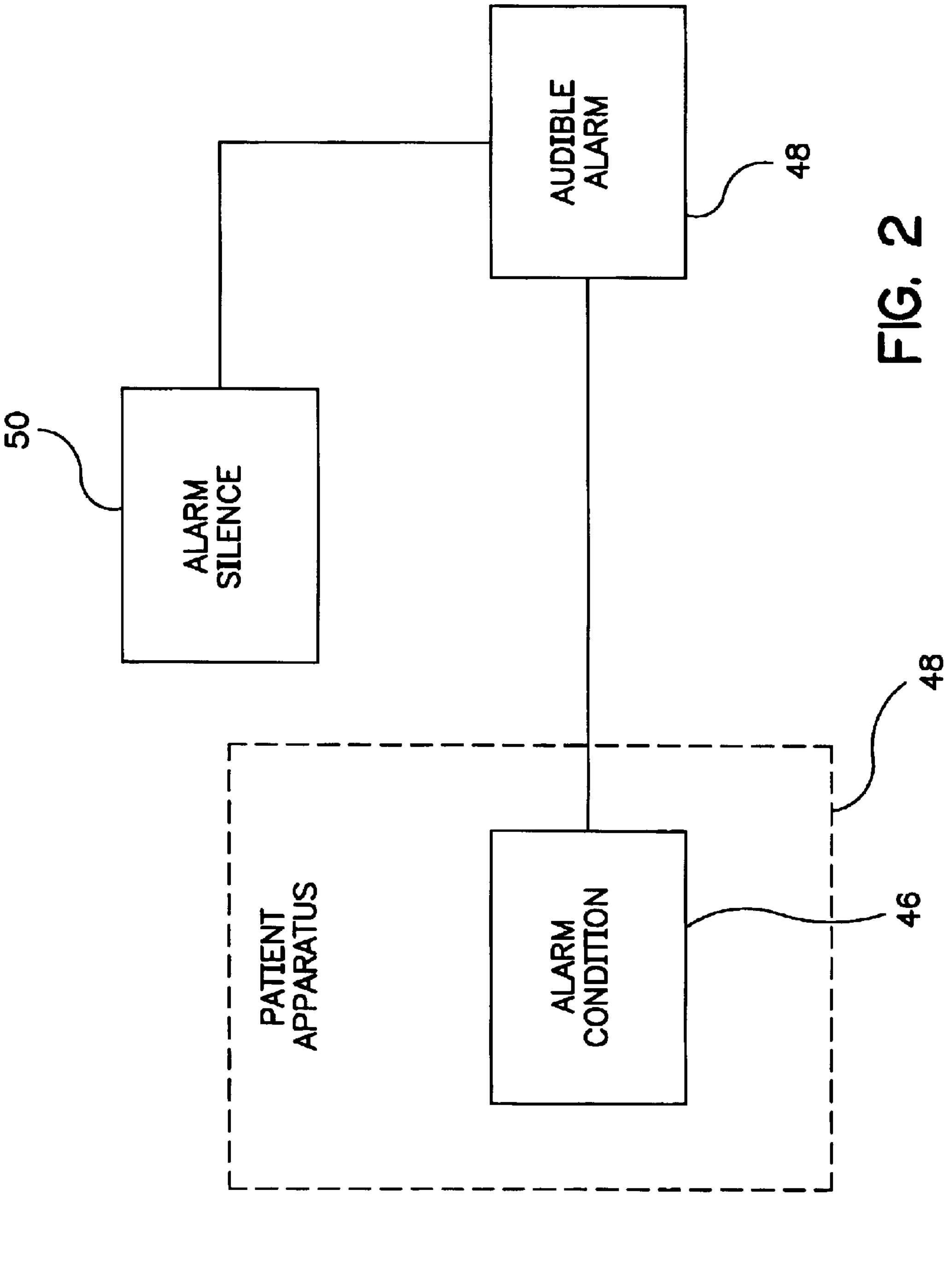
FIG. 2 is a block diagram of an electrical scheme to carry out the present invention.

Turning now briefly to FIG. 2, there is shown a block diagram of a typical electrical circuit to carry out the present invention. In FIG. 2, there can be seen a patient care apparatus 44 and which may be one of a wide variety of differing types of apparatus serving a variety of purposes. For example, as described herein, the apparatus may be an infant care center having a radiant infrared heater, however, the apparatus may also be an anesthesia machine, infusion pump, ventilator, neonatal intensive care unit or patient monitor, either incorporated into a patient care apparatus or a stand alone monitor, the main emphasis being that such patient care apparatus be located in an environment where a care provider is likely to be operating in sterile conditions and therefore is stressed and inconvenienced to be required to remove sterile gloves to physically push an alarm silence button to stop the further emitting of the audible sound and then need to re-glove to return to whatever procedure that the care provider was performing.

Associated with the patient care apparatus 44 is an alarm condition sensor 46 that continuously monitors a particular parameter and determines when an alarm condition exists, that is, when the sensed parameter is outside certain alarm limits generally established by the care provider or the manufacturer of the apparatus. That alarm condition sensor 46 may be sensing an alarm condition associated with a patient or may be a particular parameter of the patient care apparatus 44 itself. Thus, for example, if the patient care apparatus is an oximeter, there may be an alarm setting that activates an audible alarm if the oxygen saturation of the patient exceeds or falls below a certain range of values. As another example and as previously discussed herein, in the case of an infant care center, there may be an alarm that is activated if the infant skin temperature is more that a certain predetermined temperature range above or below an established or set value. In addition, with an infant care apparatus, there is normally an alarm that is activated if the set range of power to the radiant heater is left above a predetermined level for a predetermined period of time. The aforementioned alarm conditions are merely typical of some of the alarm conditions that can be seen by the alarm condition sensor 46 to determine that an alarm condition exists.

The sensing of an alarm condition by the alarm condition sensor 46 thereupon sends a signal to an audible alarm sounding device 48, such as a speaker, that emits a sound indicative of the presence of an alarm condition to alert the care providers in the immediate area of the existence of an alarm condition so that appropriate action can be taken. As noted, often the alarm condition sensed is not a critical alarm condition and the care provider only needs to be warned of the presence of that alarm condition and, therefore, the care provider is basically only interested in having knowledge of the alarm condition and to shut off the rather distracting sound of the audible alarm sounding device 48. Under those conditions, the care provider can simply activate the alarm silence switch 50 to deactivate the audible sound emanating from the audible alarm sounding device 48. At the same time, normally, the alarm silence switch 50 initiates a timer that reinstates and reactivates the audible alarm after a predetermined period of elapsed time so that the care provider is again reminded of the continued presence of the alarm condition. As such, the care provider must activate the alarm silence switch 50 multiple times for so long as the alarm condition lasts so that there is a continual reminder of the existence of that alarm condition. With the present invention, however, the care provider can continually silence the audible alarm sounding device 48 without going through the nuisance and the attention distracting procedures of de-gloving and re-gloving so that the care provider is not disrupted from continuing an ongoing procedure.

Those skilled in the art will readily recognize numerous adaptations and modifications which can be made to the non-contact alarm silence switch and method of use thereof which will result in an improved system and method yet all of which will fall within the scope and spirit of the present invention as defined in the following claims. Accordingly, the invention is to be limited only by the following claims and their equivalents.

We claim:

1. A patient care apparatus for use in the medical treatment of a patient, said patient care apparatus comprising a surface for supporting a patient, means to sense an alarm condition indicative of a parameter of the apparatus or a condition of a patient supported on said surface, an audible alarm sounding device mounted on said patient care apparatus, means responsive to the sensed alarm condition to cause said audible alarm sounding device to produce an audible sound, and a non-hand contact alarm silence switch mounted within the patient care apparatus operable by a care provider for silencing the alarm sounding device, said non-hand contact alarm silence switch being activatable without physical contact by a hand of a care provider.

2. A patient care apparatus for use with a patient as defined in claim 1 wherein said alarm silence switch is activated by an object or portion of a care provider being positioned in close proximity to said switch.

3. A patient care apparatus for use with a patient as defined in claim 2 wherein said alarm silence switch utilizes radar to detect an object.

4. A patient care apparatus for use with a patient as defined in claim 1 wherein said alarm silence switch is activated by means of optical sensing to detect an object in proximity to said switch.

5. A patient care apparatus for use with a patient as defined in claim 1 wherein said alarm silence switch is activated by means of temperature sensing to detect an object in proximity to said switch.

6. A patient care apparatus for use with a patient as defined in claim 1 wherein said alarm silence switch comprises an air motion sensor adapted to sense a change in air pressure.

7. A patient care apparatus for use with a patient as defined in claim 1 wherein said alarm silence switch comprises a sound recognition system responsive to the voice of a person.

8. A patient care apparatus for use with a patient as defined in claim 1 wherein said patient care apparatus comprises an infant care apparatus having a warmer to provide heat to an infant.

9. A patient care apparatus for use with a patient as defined in claim 1 wherein said alarm silence switch is operated by contact with a foot of a care provider.

10. A patient care apparatus as defined in claim 1 wherein the medical care of a patient is carried out under sterile conditions.

11. A system for silencing an audible alarm of a patient care apparatus having a surface to support a patient undergoing medical treatment without contact by a user, said system comprising an audible alarm device mounted on the patient care apparatus, a sensor activatable by the presence of an alarm condition indicative of a parameter of the apparatus or a condition of a patient supported on the surface to send a signal to the audible alarm device to produce an audible alarm indicative of the alarm condition and a non-hand contact alarm silence switch mounted within the patient care apparatus adapted to be activated without physical contact with a hand of a care provider to disable said audible alarm device to silence the audible alarm.

12. A system for silencing an audible alarm as defined in claim 11 wherein said patient care apparatus is an infant warmer.

13. A system for silencing an audible alarm as defined in claim 12 wherein said non contact alarm silence switch is sensitive to motion and is adapted to be activated by a object or portion of a care provider positioned in close proximity to the alarm silence switch.

14. A system for silencing an audible alarm as defined in claim 12 wherein said non-contact alarm silence switch is activated by the motion of air.

15. A system for silencing an audible alarm as defined in claim 12 wherein said non-contact alarm silence switch is activated by an audible sound.

16. A system for silencing an audible alarm as defined in claim 15 wherein said non-contact alarm silence switch is activated by the volume of the audible sound.

17. A system for silencing an audible alarm as defined in claim 11 wherein said alarm condition is a monitored parameter of the patient care apparatus.

18. A method of silencing the audible alarm on a patient care apparatus for treating a patient, said method comprising the steps of:

providing a medical apparatus for treating or monitoring a patient having a surface for supporting a patient, providing an audible alarm device mounted to the medical apparatus responsive to a predetermined condition associated with a patient or a parameter of the medical apparatus to produce an audible alarm, providing an alarm silence switch mounted to the medial apparatus activatable to silence the audible sound emanating from the audible alarm device, activating the alarm silence switch to silence the audible sound by an action of a user without physically touching the alarm silence switch by a hand of a care provider.

19. A method as defined in claim 18 wherein the step of activating the alarm silence switch comprises a user physically bringing an object or body part in close proximity to the alarm silence switch.

20. A method as defined in claim 18 wherein the step of activating the alarm silence switch comprises a user creating a motion of air in proximity to the alarm silence switch.

21. A method as defined in claim 18 wherein the step of activating the alarm silence switch comprises a user issuing a verbal command to the alarm silence switch.

22. A method as defined in claim 18 wherein the step of providing a medical apparatus for treating or monitoring a patient comprises providing an infant care apparatus.

23. A method as defined in claim 18 wherein the step of activating the alarm silence switch comprises touching the alarm silence switch by the foot of a care provider.

* * * * *